United States Patent [19]
Fukuhara

[11] Patent Number: 5,763,649
[45] Date of Patent: Jun. 9, 1998

[54] PROCESS FOR PRODUCING AROMATIC CARBOXYLIC ACIDS

[75] Inventor: Hiroshi Fukuhara, Iwakuni, Japan

[73] Assignee: Mitsui Petrochemical Industries, Ltd., Tokyo, Japan

[21] Appl. No.: 890,001

[22] Filed: Jul. 8, 1997

[30] Foreign Application Priority Data

Jul. 12, 1996 [JP] Japan ................... 8-183886

[51] Int. Cl.$^6$ ................................ C07C 51/265
[52] U.S. Cl. ................................ 562/416
[58] Field of Search ................................ 562/416

[56] References Cited

U.S. PATENT DOCUMENTS 5,371,283 12/1994 Kingsley et al. ............ 562/416

OTHER PUBLICATIONS

Japanese Abstract Only JP-A-2-134344, May 23, 1990.

Primary Examiner—Samuel Barts
Attorney, Agent, or Firm—Birch, Stewart, Kolasch & Birch, LLP

[57] ABSTRACT

A process for producing aromatic carboxylic acids by subjecting an aromatic compound having one or more substituent alkyl groups and/or partially oxidized substituent alkyl groups to a liquid phase oxidation with a molecular oxygen-containing gas in a reaction solvent containing a lower aliphatic carboxylic acid in the presence of a catalyst composed of a heavy metal compound and a bromine compound, under a condition of a weight proportion of said reaction solvent to said aromatic compound within the range from 6.5 to 70 parts by weight per one part by weight of said aromatic compound, a reaction time within the range from 45 to 4.5 minutes and a product of the numerical value of said weight proportion of the reaction solvent to the aromatic compound multiplied by the numerical value of said reaction time expressed in munute within the range from 270 to 330. The process can facilitate the diffusion of oxygen into the reaction medium and improve the volumetric efficiency of the reactor to thereby attain an efficient production of aromatic carboxylic acids with a high productivity.

7 Claims, 1 Drawing Sheet

PROCESS FOR PRODUCING AROMATIC CARBOXYLIC ACIDS

FIELD OF THE INVENTION

The present invention relates to a process for producing aromatic carboxylic acids by a liquid phase oxidation of an aromatic compound having one or more substituent alkyl groups and/or partially oxidized substituent alkyl groups.

BACKGROUND OF THE INVENTION

Aromatic carboxylic acids are important as basic chemicals and are useful in particular as the starting materials for, such as, textiles, resins and plasticizers. For instance, terephthalic acid have found its increased demand in recent years as raw stock for polyesters.

Heretofore, aromatic carboxylic acids have been produced generally by a process comprising subjecting a methyl-substituted aromatic compound to a liquid phase oxidation in a reaction solvent containing a lower aliphatic carboxylic acid, such as acetic acid, with a molecular oxygen-containing gas in the presence of a catalyst composed of a heavy metal compound and a bromine compound. In such a conventional production process, the reaction solvent is used usually in an amount of 2–6 parts by weight per one part by weight of the aromatic compound used as the starting material to be oxidized (See Japanese Patent Kokai No. 63-288309 A). In a continuous production, the residence time of the aromatic compound in the reactor is usually in the range of 40–150 minutes.

In such a conventional process for producing aromatic carboxylic acids, the reaction mixture in the reactor will contain a large amount of the resulting aromatic carboxylic acid as a co-existing solid matter, so long as the resulting aromatic carboxylic acid is insoluble in the reaction solvent, since the proportion of the reaction solvent used to the starting material to be oxidized is not sufficiently high. For instance, for producing terephthalic acid from p-xylene in a reaction solvent used in an amount as above, the concentration of terephthalic acid in the reaction slurry may be 20–40% by weight, co-existing as solid.

Thus, in the conventional process for producing aromatic carboxylic acids, the oxidation product will be present in a large amount within the reactor in the form of a solid which does not participate in promoting the oxidation reaction, obstructing the gas/liquid contact of the molecular oxygen-containing gas with the lower aliphatic carboxylic acid solvent. Accordingly, the dissolution efficiency of molecular oxygen in the gas into the reaction solvent is decreased.

Moreover, the existence of a large amount of solid matter in the reactor does mean a decrease in the effective reaction volume within the reactor, rendering a reverse effect to any improvement in the productivity of the aromatic carboxylic acid.

Japanese Patent Kokai No. 61-112044 A (corresponding to U.S. Pat. No. 4,777,287) discloses a process for producing aromatic carboxylic acids by a liquid phase oxidation of an alkyl-substituted aromatic compound with a molecular oxyge-containing gas. It is described therein that the amount of the reaction solvent used is in the range from 1 to 10, preferably from 2 to 6 parts by weight per one part by weight of the raw material to be oxidized and the residence time of the reaction slurry in the reactor is in the range from about 20 to about 90 minutes.

This prior technique disclosed in the above patent gazette, however, concerns a technical measure for increasing the processed amount of the raw material to be oxidized under a condition of comparatively lower temperature and lower pressure and does not include any suggestion for positively combining a condition of larger amount of the reaction solvent to be used with a condition of shorter reaction time for the oxidation. It does also include no suggestion as to a fact that a high quality aromatic carboxylic acid may be produced efficiently when the product of the amount of reaction solvent to be used multiplied by the reaction time is within a specific range.

SUMMARY OF THE INVENTION

An object of the present invention is to obviate the above-mentioned problems in the prior art of production of aromatic carboxylic acids and to provide a process for producing aromatic carboxylic acids, which can afford to promote the diffusion of molecular oxygen into the reaction solvent while improving the volume efficiency of the reactor to thereby make possible to produce a high quality aromatic carboxylic acid efficiently at a high productivity.

The inventors have found in the course of their sound researches for solving the above inventive object that the aromatic compound used as the raw material can be oxidized within a very short time. The present invention was based on such an experienced knowledge, whereby a revolutionary invention which was never seen in the past concerning a process for producing aromatic carboxylic acids as described below has been completed by the inventors.

The process for producing aromatic carboxylic acids by a liquid phase oxidation of an aromatic compound according to the present invention comprises subjecting an aromatic compound having one or more substituent alkyl groups and/or partially oxidized substituent alkyl groups to a liquid phase oxidation with a molecular oxygen-containing gas in a reaction solvent containing a lower aliphatic carboxylic acid in the presence of a catalyst composed of a heavy metal compound and a bromine compound, under the reaction condition of a weight proportion of said reaction solvent to said aromatic compound having one or more substituent alkyl groups and/or partially oxidized substituent alkyl groups in the liquid phase within the range from 6.5 to 70 parts by weight per one part by weight of said aromatic compound having one or more substituent alkyl groups and/or partially oxidized substituent alkyl groups, a reaction time within the range from 45 to 4.5 minutes and a mathematical product of the numerical value of said weight proportion of said reaction solvent to said aromatic compound having one or more substituent alkyl groups and/or partially oxidized substituent alkyl groups multiplied by the numerical value of said reaction time expressed in minute within the range from 270 to 330.

In this specification, the "weight proportion of the reaction solvent to the starting aromatic compound to be oxidized" is termed "solvent weight ratio". For example, a solvent weight ratio of 10 means that ten parts by weight of the reaction solvent are employed per one part by weight of the starting aromatic compound to be oxidized.

DETAILED DESCRIPTION OF THE INVENTION

Figure 1:
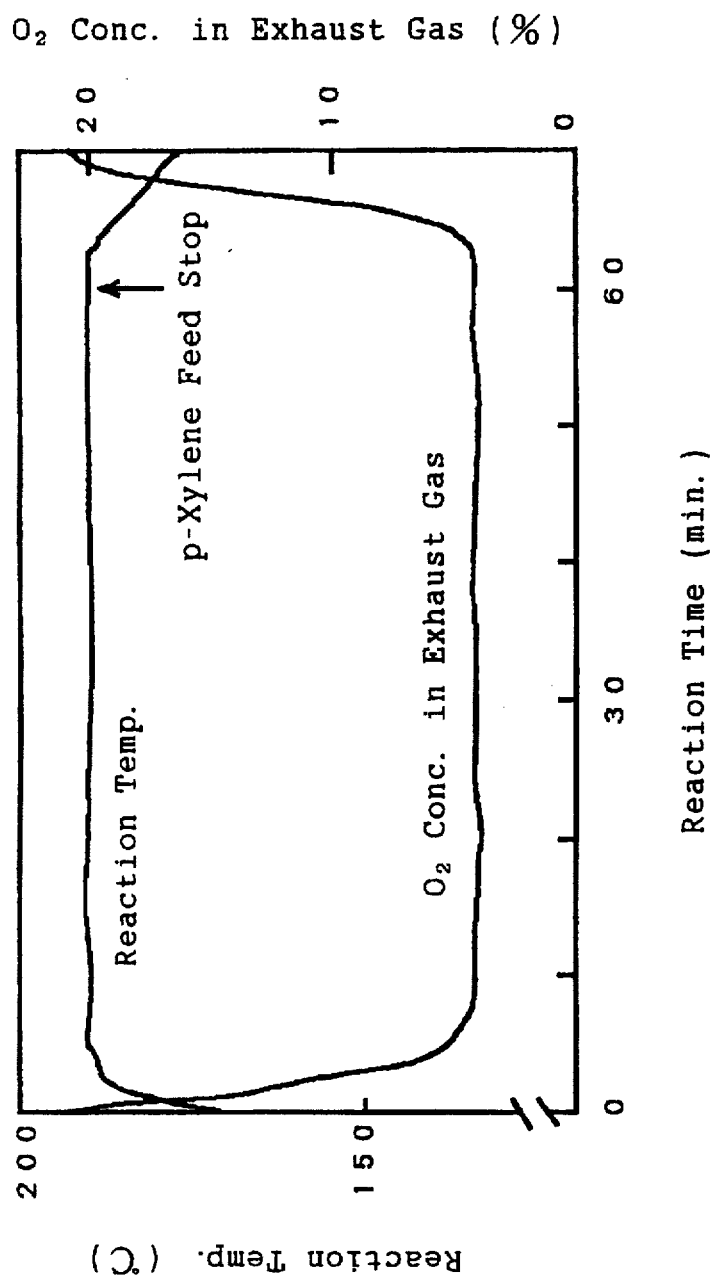
FIG. 1 is a graph showing the relationship between the reaction time and the reaction temperature or the concentration of $O_2$ in the exhaust gas during a semicontinuous oxidation of p-xylene.

As the starting material to be oxidized for the production of the aromatic carboxylic acid according to the present invention (sometimes denoted hereinafter simply as oxidation raw material), aromatic compounds having one or more alkyl substituent groups and/or partially oxidized alkyl substituent groups may be employed. Such aromatic compounds may be of monocyclic or polycyclic. As the alkyl substituent group, there may be enumerated, for example, alkyl groups having 1–4 carbon atoms, such as, methyl, ethyl, n-propyl, isopropyl and the like. As the partially oxidized alkyl group, for example, formyl group, acyl groups, carboxyl group and hydroxyalkyl groups, may be enumerated.

Concrete examples of the aromatic compound having one or more alkyl substituent groups include di- or polyalkylbenzenes having 2–4 alkyl groups of 1–4 carbon atoms, such as, m-diisopropylbenzene, p-diisopropylbenzene, m-cymene, p-cymene, m-xylene, p-xylene, trimethylbenzene and tetramethylbenzene; di- or polyalkylnaphthalenes having 2–4 alkyl groups of 1–4 carbon atoms, such as, dimethylnaphthalene, diethylnaphthalene, diisopropylnaphthalene and the like; polyalkylbiphenyls having 2–4 alkyl groups of 1–4 carbon atoms, such as dimethylbiphenyl and the like.

The aromatic compounds having one or more partially oxidized alkyl groups are those in which one or more alkyl substituent groups of the above-mentioned alkyl substituent-containing aromatic compounds are partially oxidized into formyl, acyls, carboxyl or hydroxyalkyls. Concrete examples thereof include 3-methylbenzaldehyde, 4-methylbenzaldehyde, m-toluic acid, 3-formylbenzoic acid, 4-formylbenzoic acid and formylnaphthalenes. They may be used solely or in a mixture of two or more of them.

In the process according to the present invention, a catalyst system composed of a heavy metal compound and a bromine compound is employed. Concrete examples of these compounds may be as follows. As the heavy metal for the heavy metal compound, there may be enumerated, for example, cobalt, manganese, nickel, chromium, zirconium, copper, lead, hafnium and cerium. They may be used solely or in a combination, wherein a combination of cobalt and manganese is particularly preferred.

As the compound of such a heavy metal, there may be enumerated, for example, acetate, acetylacetonate, naphthenate, stearate and bromide, wherein special preference is given to acetate.

As the bromine compound, there may be enumerated, for example, inorganic bromides, such as, molecular bromine, hydrogen bromide, sodium bromide, potassium bromide, cobalt bromide and manganese bromide; and organic bromine compounds, such as, methyl bromide, methylene bromide, bromoform, benzyl bromide, bromomethyltoluene, dibromoethyltoluene, tribromoethane and tetrabromoethane. These bromine compounds may also be used solely or in a mixture of two or more of them.

According to the present invention, the catalyst constituted of the combination of the above-mentioned heavy metal compound and the above-mentioned bromine compound may preferably be of those combinations in which one mole of the heavy metal compound is combined with 0.05–10 moles, preferably 0.1–2 moles of the bromine compound. Such a catalyst may be used usually in an amount in the range from 10 to 10,000 ppm, preferably from 100 to 5,000 ppm as the heavy metal concentration in the reaction solvent.

In the process according to the present invention, the aromatic compound as the starting material is oxidized into the aromatic carboxylic acid as the product by a liquid phase oxidation in a reaction solvent containing a lower aliphatic carboxylic acid with a molecular oxygen-containing gas in the presence of the above-mentioned catalyst.

As the molecular oxygen-containing gas, for example, oxygen gas or air may be used, wherein air is preferable for the practical use. The molecular oxygen-containing gas may be supplied to the reaction system in excess over the requisite amount for the oxidation of the starting aromatic compound into an aromatic carboxylic acid. When air is emloyed as the molecular oxygen-containing gas, it is preferable to supply air to the reaction system in a proportion of 2–20 $Nm^3$, preferably 2.5–15 $Nm^2$ per 1 kg of the starting aromatic compound to be oxidized.

Concrete examples of the lower aliphatic carboxylic acid to be used as the reaction solvent include acetic acid, propionic acid and butyric acid. The lower aliphatic carboxylic acid may be used either solely or in a mixture with water for the reaction solvent. Concrete examples of the reaction solvent include acetic acid, propionic acid, butyric acid and mixtures of them as well as mixtures of such a lower aliphatic carboxylic acid with water. Among them, preference is given to the mixture of acetic acid with water, wherein a mixture of 1–20 parts, in particular, 5–15 parts by weight of water with 100 parts by weight of acetic acid is especially preferable.

The amount of the reaction solvent to be used may be in the range from 6.5 to 70 parts by weight, preferably from 7.5 to 50 parts by weight per one part by weight of the starting aromatic compound to be oxidized in the liquid phase in the reactor. Thus, the solvent weight ratio may be in the range from 6.5 to 70, preferably from 7.5 to 50. When the amount of the reaction solvent used is in the above-mentioned range, the diffusion of molecular oxygen into the reaction solvent can be promoted with simultaneous increase in the reaction space within the reactor, since the solid concentration in the reaction mixture can be maintained low, so that a high reaction rate can be attained with simultaneous attainment of an efficient production of the higher quality aromatic carboxylic acid. Due to the attainment of a higher reaction rate, it is also possible to attain a higher feed rate of the starting aromatic compound with a shorter reaction time, whereby the volume efficiency of the reactor becomes higher with an increase in the productivity.

In the process according to the present invention, the reaction time is adjusted within the range from 45 to 4.5 minutes, preferably from 40 to 6 minutes. Here, the reaction time means the residence time in the reactor, when the oxidation is effected in a continuous manner. By adjusting the reaction time within the above-mentioned range, a high quality aromatic carboxylic acid can be produced efficiently even if the amount of the reaction solvent used is in the range as mentioned above.

Though the above-mentioned reaction time is substantially short as compared with that of the prior technique, the oxidation can proceed sufficiently within the above-mentioned reaction time. Thus, when the liquid phase oxidation is effected while feeding the starting aromatic compound (p-xylene) and air to the reaction system continuously, as shown in the appended FIG. 1, the oxygen concentration in the exhaust gas will increase after few minutes from the cessation of feeding of the aromatic compound. The discovery of such a phenomenon is attributed exclusively to the inventor, which shows that a shorter reaction time may be permitted.

In the process according to the present invention, the solvent weight ratio is held in a combination with the reaction time such that the mathematical product of the numerical value of the solvent weight ratio multiplied by the numerical value of the reaction time expressed in minute is within the range from 270 to 330, preferably from 290 to 310. In case the above-mentioned mathematical product is within the above range, a high quality aromatic carboxylic acid can be produced at a high productivity.

The reaction temperature during the oxidation may desirably be, in general, in the range from 100° to 250° C., preferably from 150° to 220° C. Such a pressure in the reactor during the oxidation may be enough, that the reaction system is maintained in a liquid phase.

By performing the reaction in the condition as given above, an aromatic carboxylic acid corresponding to the starting aromatic compound to be oxidized can be obtained. Concrete examples of the aromatic carboxylic acid include aromatic dicarboxylic acids, such as, terephthalic acid, isophthalic acid, 2,6-naphthalene dicarboxylic acid and 1,6-biphenyl dicarboxylic acid; aromatic tricarboxylic acids, such as, trimellitic acid and trimesic acid; and aromatic polycarboxylic acids, such as, pyromellitic acid and so on.

It is desirable to apply the process according to the present invention to the production of aromatic dicarboxylic acids and aromatic carboxylic acids which are insoluble or scarcely soluble in the reaction solvent, especially to the production of terephthalic acid.

In the process according to the present invention, the resulting aromatic carboxylic acid is isolated from the reaction mixture usually by means of a solid/liquid separation technique. The solid/liquid separation may desirably be realized at a temperature which is the same as that of the oxidation reaction or close thereto. Concretely, the solid/liquid separation may desirably be realized at a temperature within the range from a temperature which is by 30° C. lower than the oxidation temperature to a temperature which is by 10° C. higher than the oxidation temperature, preferably from a temperature which is by 20° C. lower than the oxidation temperature to a temperature which is by 5° C. higher than the oxidation temperature. By performing the separation of the resulting aromatic carboxylic acid from the reaction mixture at a temperature as given above, any adhesion of intermediate products having lower solubility in the reaction solvent and colored impurities onto the product crystals by deposition thereon due to possible temperature decrease can be avoided, permitting to obtain a high quality aromatic carboxylic acid.

For effecting the solid/liquid separation of the resulting solid aromatic carboxylic acid from the reaction mixture under the condition of high temperature and high pressure, any apparatus can be employed without any specific restriction, so long as it allows to maintain the temperature of the reaction mixture within the range as given above. Thus, there may be employed, for example, a pressurizable filter in which the contents can be pressurized and can be heated and a hydrocyclone.

It is preferable in the process according to the present invention, that a part or the whole of the reaction mother liquor obtained by the solid/liquid separation of the reaction mixture is returned as such to the reactor. Here, it is also possible to rely upon such a technique as effecting the reaction under the above-mentioned condition of the solvent weight ratio, the reaction time and the mathematical product and subjecting the resulting reaction mixture having lower solid product concentration to a thickening of the solid product by means of a pertinent apparatus, such as a hydrocyclone, whereupon the thereby separated liquid phase is returned to the reactor, while further treating the thickened slurry in an ordinary solid/liquid separation unit. Employment of such a technique is particularly preferable, since a slurry of higher solid product concentration can be fed to the ordinary solid/liquid separation unit even if the oxidation in the reactor is carried out with a lower solid product concentration and, in this manner, it is made possible to avoid any necessity of dealing with a large amount of reaction mixture having a lower solid product concentration.

Concrete manner for performing the oxidation in the process according to the present invention is not specifically restricted and either of batchwise method, semicontinuous method and continuous method can be incorporated. Among them, continuous and semicontinuous methods are preferred and, in particular, continuous method is preferable.

The process according to the present invention permits to produce a high quality aromatic carboxylic acid in an efficient manner, since the diffusion of oxygen molecules into the reaction solvent is promoted and the reaction space available for the oxidation is increased due to the fundamental design permitting use of large amount of the reaction solvent as compared with the prior technique. This technical advantage of capability of obtaining an aromatic carboxylic acid of high quality does mean a very significant industrial importance. Namely, an intrinsic function of an industrial production apparatus is to provide a product while maintaining its quality reliably and, therefore, it is required for a production apparatus to produce the product while maintaining the predetermined product quality in an economical manner. It is possible by the process according to the present invention to achieve an economical low-cost production while maintaining the predetermined product quality.

In conclusion, it is made possible by the process according to the present invention to promote the diffusion of oxygen molecules into the reaction solvent with simultaneous attainment of improvement in the volumetric efficiency of the reactor, whereby aromatic carboxylic acids of high quality can be produced efficiently at a high productivity.

DESCRIPTION OF THE PREFERRED EMBODIMENTS

Below, the present invention is further described by way of Examples and Comparartive Examples.

Example 1

In an autoclave made of titanium having an inner diameter of 66 mm, a depth of 168 mm and a capacity of 500 ml and equipped with a stirrer, a reflux condenser and a pressure control valve, 215 g of acetic acid containing water at a concentration of 5.9% by weight, 0.54 g of cobalt acetate tetrahydrate, 0.26 g of manganeseacetate tetrahydrate and 0.45 g of a 47 wt. % aqueous solution of hydrogen bromide were charged. The contents of the autoclave were heated to 190° C. while maintaining the internal pressure at 1.37 MPa (gauge pressure). When the temperature of the contents had reached at 190° C., air was fed thereinto at a rate of 2.83N liters per minute with powerful agitation of the contents, while feeding p-xylene thereto at a rate of 0.83 ml/min. by a metering pump, in order to effect a liquid phase oxidation of p-xylene. The feeding of p-xylene was continued for 45 minutes.

After termination of the feeding of p-xylene, the feeding of air thereinto was stopped at the occasion of appearing of increase in the oxygen concentration in the exhaust gas from the autoclave. It took about three minutes from the stoppage of feeding of p-xylene till the stoppage of feeding of air. After the autoclave had been cooled to room temperature, the contents of the autoclave was taken out and filtered to separate the product crystals, whereupon the crystals were sufficiently washed with acetic acid and water before being dried. The yield and the quality of the so-obtained terephthalic acid are recited in Table 2.

Examples 2 and 3

As shown in Table 1, the procedures of Example 1 were repeated except that the p-xylene feed time was changed to 30 minutes or 20 minutes, respectively. The results are summarized also in Table 2.

Comparative Examples 1 and 2

As shown in Table 1, the procedures of Example 1 were repeated except that the p-xylene feed time was changed to 60 minutes or 80 minutes, respectively. The results are summarized also in Table 2.

TABLE 1

| Examples or Comp. Examples | p-Xylene Feed Time (A) (min.) | Solvent Wt. Ratio (B)[1] | A × B[2] | Slurry Conc. over Oxidation (wt. %) |
|---|---|---|---|---|
| Ex. 1 | 45 | 6.6 | 297 | 17.5 |
| Ex. 2 | 30 | 10 | 300 | 12.6 |
| Ex. 3 | 20 | 15 | 300 | 8.7 |
| C. Ex. 1 | 60 | 5 | 300 | 21.8 |
| C. Ex. 2 | 80 | 3.7 | 296 | 26.6 |

Notes:
[1] Solvent weight ratio, namely the weight proportion of the charged acetic acid solvent to one part by weight of p-xylene fed.
[2] The product of the numerical value of the solvent weight ratio multiplied by the numerical value of the reaction time in minute.

TABLE 2

| Examples or Comp. Examples | Terephthalic Acid Yield (%)[3] | Content of 4-CBA in TA (ppm)[4] | Transmittance of TA ($T_{340}$) (%)[5] |
|---|---|---|---|
| Ex. 1 | 93.7 | 1600 | 32.4 |
| Ex. 2 | 93.1 | 1360 | 41.9 |
| Ex. 3 | 94.3 | 1230 | 55.6 |
| C. Ex. 1 | 93.9 | 1970 | 18.4 |
| C. Ex. 2 | 93.9 | 2560 | 14.1 |

Notes:
[3] Yield of terephthalic acid, based on molar yield with respect to the fed p-xylene.
[4] Content of 4-carboxybenzaldehyde in terephthalic acid (TA).
[5] Transmittance ($T_{340}$) of terephthalic acid determined with a solution prepared by dissolving 7.5 g of the resulting TA in 50 ml of 2N KOH aqueous solution at a wave length of 340 nm, which serves as a parameter of the hue of the TA product.

Example 4

The procedures of Example 1 were repeated except that the air feed rate was changed to 3.39N liters per minute and the p-xylene feeding was effected at a rate of 1.0 ml/min for 20 successive period with further continued oxidation for a period of 5 minutes thereafter (a total reaction time of 25 minutes). Here, the solvent weight ratio was 12.5, the residence time was 25 minutes and the product of these values was 313. It was found that the yield of terephthalic acid was 92.7%, the 4-CBA content in this terephthalic acid product was 2210 ppm and the transmittance ($T_{340}$) of this terephthalic acid product was determined to be 30.5%.

Comparative Example 3

The titanium autoclave used in Example 1 was furnished now with a reaction mixture withdrawal nozzle and was connected to a 500 ml pressure receiver equipped with a stirrer and a reflux condenser. In this autoclave, 215 g of acetic acid containing water at a concentration of 5.9 wt. %, 0.54 g of cobalt acetate tetrahydrate, 0.26 g of manganese acetate tetrahydrate and 0.45 g of a 47 wt. % aqueous solution of hydrogen bromide were charged. The inner pressure of the autoclave was pressurized to 1.57 MPa (gauge pressure) and heating of the contents was started. When the temperature of the contents had reached at 190° C., air was fed thereinto at a rate of 2.39N liters per minute with powerful agitation of the contents, while feeding of p-xylene thereto at a rate of 0.70 ml/min. by a metering pump and feeding of a catalyst solution composed of 0.54 part by weight of cobalt acetate tetrahydrate, 0.26 part by weight of manganese acetate tetrahydrate, 0.45 part by weight of 47 wt. % aqueous solution of hydrogen bromide, 12.7 parts by weight of water and 202.3 parts by weight of acetic acid thereto at a rate of 2.86 ml/min. by another metering pump are started, in order to effect a liquid phase oxidation of p-xylene.

The withdrawal of the reaction mixture was realized intermittently by increasing the internal pressure of the autoclave at a periodic interval by closing the magnetic cutoff valve disposed at an upper portion of the cooling pipe for the exhaust gas from the autoclave periodically. The reaction mixture collected in the pressure receiver was withdrawn at a predetermined periodic interval into a glass receiver all at once. The amount of the reaction mixture withdrawn at each one hour period was about 233.3 g in average. From the withdrawn reaction mixture, the product crystals were filtered off and were washed with acetic acid and water sufficiently before being dried.

After proceeding with three hours' continuous reaction, the reaction mixture obtained in a stable condition was processed by an aftertreatment to obtain a terephthalic acid product, which was analysed for its quality. The 4-CBA content in the product was found to be 1830 ppm and the transmittance ($T_{340}$) was observed to be 62%. The reaction condition was recited in Table 3.

Examples 5 and 6

The procedures of Comparative Example 3 were repeated except that the feed rate of the catalyst solution was changed either to 4.29 ml/min. or 5.72 ml/min., respectively, and the amount of the reaction mixture withdrawn was correspondingly increased. The results obtained were as given in Table 3.

TABLE 3

| Examples or Comp. Examples | Residence Time (A) (min.) | Solvent Wt. Ratio (B)[1] | A × B[2] | TPA Quality[3] 4-CBA Content (ppm) | $T_{340}$ (%) |
|---|---|---|---|---|---|
| C. Ex. 3 | 60 | 5 | 300 | 1830 | 62 |
| Ex. 5 | 40 | 7.5 | 300 | 1440 | 66 |
| Ex. 6 | 30 | 10 | 300 | 1560 | 66 |

Notes:
[1] See note 1) of Table 1.
[2] See note 2) of Table 1.
[3] See notes 4) and 5) of Table 2.

Example 7

Oxidation of p-xylene was carried out under the same condition as in Example 5 using a continuous production arrangement composed of a one liter reactor made of titanium provided with a stirrer, a gas cooling pipe, a nozzle for feeding air into the reactor, a feed line for feeding the starting aromatic compound and a reaction mixture withdrawal exit at the bottom; a high temperature pressurizable filter of a capacity of 500 ml made of titanium provided at its bottom with a stainless steel filter; a one liter titanium receiver for receiving the reaction mother liquor discharged from the pressurizable filter; and a pressure receiver (1 liter, Hastelloy C) for receiving the slurry from the reactor without passing through the pressurizable filter. The withdrawal of the slurry from the reactor was initially effected into the pressure receiver made of Hastelloy C until a stable reaction mixture was obtained. During this period, the temperature of the outer wall of the high temperature pressurizable filter was adjusted within the range from 185° to 190° C. to prepare for starting up the pressure filtration.

After two hours' continuous reaction, the withdrawal of the slurry from the reactor was changed into the pressurizable filter by changing the valve in the slurry withdrawal line to the side of the pressurizable filter. The slurry was then allowed to accumulate in the pressurizable filter and was subjected to a pressure filtration. The resulting solid product was washed with acetic acid and water before being dried.

This product was analysed, whereby it was found that the 4-CBA content was 1250 ppm and the transmittance at 340 nm ($T_{340}$) was observed to be 71%. The results are summarized in Table 4.

Example 8

The procedures of Example 7 were repeated except that the solvent weight ratio and the residence time were changed to 15 and to 20 minutes, respectivly. The 4-CBA content of the resulting product was found to be 1100 ppm and the transmittance ($T_{340}$) was observed to be 74%. The results are summarized in Table 4.

Examples 9 to 12 and Comparative Examples 4 to 9

Using the continuous production arrangement used in Example 7, terephthalic acid was produced in the manner as follows:

A catalyst solution was prepared by mixing 4.29 g of cobalt acetate tetrahydrate, 2.10 g of manganese acetate tatrahydrate, 3.69 g of 47 wt. % aqueous solution of hydrogen bromide and 81.7 g of water with 2.058 g of acetic acid. The oxidation reactor was charged with 450 g of this catalyst solution and nitrogen gas was impressed thereinto before heating was started. Air feeding into the reactor was started at the occasion of arrival of the reactor internal temperature to a temperature close to 190° C. Simultaneously with the commencement of air feeding, feeding of the starting mixture prepared by mixing p-xylene with the catalyst solution in a predetermined proportion was started at a predetermined feed rate. The feeding of air and the feeding of the starting mixture into the reactor were continued while keeping the reactor internal pressure at 1.28 MPa (gauge pressure) and the reaction temperature at 190° C. The air feeding rate was adjusted so as to maintain the oxygen concentration in the exhaust gas from the reactor at 3–4 volume %. The reaction mixture was extracted successively from the reactor into the pressure receiver (mad of Hastelloy C) so that a constant amount of 450 g of the reaction mixture was held always in the reactor. When a predetermined amount of the reaction mixture had been accumulated in the pressure receiver, this was withdrawn therefrom intermittently into the normal pressure receiver. After a predetermined period of time had elapsed (about threefold of the residence time may be accounted for) and the continuous reaction had been stabilized, an aliquot of the reaction mixture was withdrawn from the reactor into the pressurizable filter and was subjected to a solid/liquid separation under a pressurized and heated condition. The crude terephthalic acid collectd in the pressurizable filter was subjected to washing with acetic acid and to washing with water before being taken out. Also for the sample withdrawn into the normal pressure receiver, a filtering operation was effected at room temperature (about 30° C.) to obtain a terephthalic acid product (TA). The experimental results of reaction carried out under varying conditions are summarized in Table 4.

TABLE 4

| Examples or Comp. Examples | Residence Time (A) (min.) | Solvent Wt. Ratio (B)[1] | A × B[2] | Filtering Temp. of TA (°C.)[3] | TA Quality[3] 4-CBA Cont. (ppm) | $T_{340}$ (%) |
|---|---|---|---|---|---|---|
| Ex. 7 | 40 | 7.5 | 300 | 190 | 1250 | 71 |
| C. Ex. 4 | 30 | 7.5 | 215 | 30 | 5200 | 40 |
| Ex. 8 | 20 | 15 | 300 | 190 | 1100 | 74 |
| C. Ex. 5 | 15 | 15 | 225 | 30 | 4170 | 41 |
| C. Ex. 6 | 15 | 15 | 225 | 190 | 1490 | 67 |
| Ex. 9 | 30 | 10 | 300 | 190 | 1170 | 72 |
| Ex. 10 | 30 | 10 | 300 | 30 | 2650 | 48 |
| Ex. 11 | 30 | 10 | 300 | 100 | 1620 | 58 |
| Ex. 12 | 30 | 10 | 300 | 150 | 1430 | 64 |
| C. Ex. 7 | 20 | 10 | 200 | 30 | 7100 | 34 |
| C. Ex. 8 | 20 | 10 | 200 | 190 | 2960 | 63 |
| C. Ex. 9 | 15 | 10 | 150 | 190 | 9300 | 52 |

Notes:
[1] See note 1) of Table 1.
[2] See note 2) of Table 1.
[3] TA = terephthalic acid.

From the above-described results, it is seen that all inventive Examples with mathematical products of solvent weight ratio values multiplied by residence time values in minute within the range specified by the present invention show that terephthalic acid products of higher quality as compared with those of Comparative Examples were obtained.

I claim:

1. A process for producing aromatic carboxylic acids by a liquid phase oxidation of an aromatic compound, comprising subjecting an aromatic compound having one or more substituent alkyl groups and/or partially oxidized substituent alkyl groups to a liquid phase oxidation with a molecular oxygen-containing gas in a reaction solvent containing a lower aliphatic carboxylic acid in the presence of a catalyst composed of a heavy metal compound and a bromine compound, under the reaction condition of a weight proportion of said reaction solvent to said aromatic compound having one or more substituent alkyl groups and/or partially oxidized substituent alkyl groups in the liquid phase within the range from 6.5 to 70 parts by weight per one part by weight of said aromatic compound having one or more substituent alkyl groups and/or partially oxidized substituent alkyl groups, a reaction time within the range from 45 to 4.5 minutes and a mathematical product of the numerical value of said weight proportion of said reaction solvent to said aromatic compound having one or more substituent alkyl groups and/or partially oxidized substituent alkyl groups multiplied by the numerical value of said reaction time expressed in minute within the range from 270 to 330.

2. A process as claimed in claim 1, wherein the resulting aromatic carboxylic acid is isolated from the reaction mixture in a state in which a condition close to the oxidation reaction is maintained.

3. A process as claimed in claim 1 or 2, wherein the resulting aromatic carboxylic acid is isolated from the reaction mixture at a temperature in the range from a temperature which is by 30° C. lower than the oxidation reaction temperature to a temperature which is by 10° C. higher than the oxidation reaction temperature.

4. A process as claimed in claim 1 or 2, wherein the reaction solvent is a mixture of acetic acid and water.

5. A process as claimed in claim 1 or 2, wherein the resulting aromatic carboxylic acid is one which is insoluble or scarcely soluble in the reaction solvent.

6. A process as claimed in claim 1 or 2, wherein the resulting aromatic carboxylic acid is an aromatic dicarboxylic acid.

7. A process as claimed in claim 1 or 2, wherein the resulting aromatic carboxylic acid is terephthalic acid.

* * * * *